US00PP36865P2

(12) United States Plant Patent
Schoemaker

(10) Patent No.: US PP36,865 P2
(45) Date of Patent: Jul. 29, 2025

(54) ***HYDRANGEA* PLANT NAMED 'LC NO23'**

(50) Latin Name: *Hydrangea arborescens*
Varietal Denomination: LC NO23

(71) Applicant: Alex Shoemaker Living Creations Holding B.V., Boskoop (NL)

(72) Inventor: Alex L. Schoemaker, Boskoop (NL)

(73) Assignee: Alex Schoemaker Living Creations Holding B.V. (NL)

( * ) Notice: Subject to any disclaimer, the term of this patent is extended or adjusted under 35 U.S.C. 154(b) by 0 days.

(21) Appl. No.: 18/950,498

(22) Filed: Nov. 18, 2024

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct cultivar of *Hydrangea arborescens* plant named 'LC NO23' is disclosed, characterized by sturdy stems on medium sized, compact plants. Panicles are semi-flattened globular in shape and dense with flowers. Plants are highly floriferous and flower from June to September. The sterile flowers have ornamental sepals that are bright white from the beginning to the end of the flower period. The new variety is a *Hydrangea*, typically produced as an outdoor ornamental plant.

2 Drawing Sheets

Figure 1:
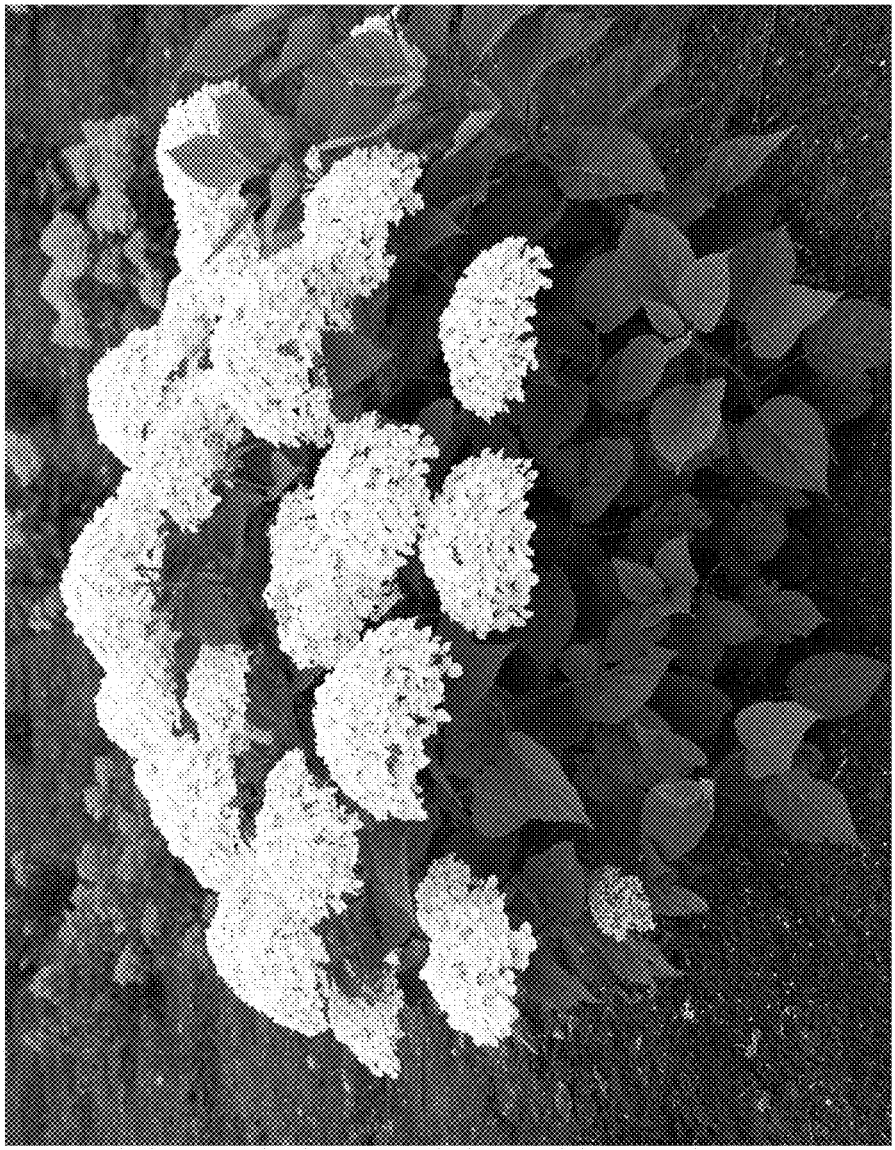

Latin name of the genus and species: *Hydrangea arborescens.*

Variety denomination: 'LC NO23'.

BACKGROUND OF THE INVENTION

The new cultivar is a product of a planned breeding program conducted by the inventor in Boskoop, the Netherlands. The inventor crossed two unnamed, unpatented proprietary seedlings in 2015. The new cultivar 'LC NO23' was selected by the inventor in 2020 from seedlings developed from the 2015 crossing.

Asexual reproduction of the new cultivar 'LC NO23' was first performed during summer of 2020 in in Boskoop, the Netherlands, by softwood cuttings. Through subsequent propagation, multiple additional generations have been reproduced, having shown that the unique features of this cultivar are stable and reproduced true to type.

The inventor has filed an application with the CPVO Nov. 20, 2023, having application number 2023/2412. This disclosure falls within the exception allowed under 102(b)(1).

SUMMARY OF THE INVENTION

The cultivar 'LC NO23' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LC NO23.' These characteristics in combination distinguish 'LC NO23' as a new and distinct *Hydrangea* cultivar:

1. Sturdy stems.
2. Medium, compact plant size.
3. Highly floriferous plants.

4. Bright white, sepals retaining bright white color from the beginning to the end of the flowering period.
5. Flowering period from June to September.
6. Semi-flattened globular, flower heads, dense with flowers.

PARENT COMPARISON

Plants of 'LC NO23' are similar to plants of both parents in most horticultural characteristics, however, plants of 'LC NO23' differ in the following:

1. Plants of the new variety are approximately 30% smaller, in both height and width at maturity than plants of either parent.
2. Flower sepals of the new variety are brighter white than sepals of either parent.

COMMERCIAL COMPARISONS

Plants of 'LC NO23' can be compared to plants of the commercial variety *Hydrangea arborescens* 'GRHYAR1406', U.S. Plant Pat. No. 31,121. Plants of 'LC NO23' are similar to plants of 'GRHYAR1406' in most horticultural characteristics, however, plants of 'LC NO23' differ in the following:

1. 'LC NO23' has slightly larger and flatter inflorescences.
2. 'LC NO23' has white mature sterile flower sepals. 'GRHYAR1406' has sterile flower sepals that are pink and white.

Plants of the new cultivar *Hydrangea* 'LC NO23' can be compared to the commercial variety *Hydrangea arborescens* 'Annabelle', unpatented. Plants of 'LC NO23' are similar to plants of 'Annabelle' in most horticultural characteristics, however, plants of 'LC NO23' differ in the following:

1. Panicles of the new variety are flatter than panicles of this comparator.
2. Stems of the new variety are stronger than stems of this comparator.

3. Plants of the new variety are 20% to 30% smaller than plants of this comparator in both height and width.

Plants of the new cultivar *Hydrangea* 'LC NO23' can be compared to the commercial variety *Hydrangea arborescens* 'Bellaragazza Blanchetta', unpatented. Plants of 'LC NO23' are similar to plants of 'Bellaragazza Blanchetta' in most horticultural characteristics, however, plants of 'LC NO23' differ in the following:

1. 'LCNO23' has bright white sterile flowers; 'Bellaragazza Blanchetta' has white flowers flushed light pink.
2. Plants of the new variety are less dwarf than plants of this comparator. Plants of the new variety are approximately 20% taller and wider than plants of this comparator.

BRIEF DESCRIPTION OF THE PHOTOGRAPHS

The accompanying photograph in FIG. 1 illustrates in full color a typical plant of 'LC NO23' grown in a field in Boskoop, the Netherlands. This plant is approximately 3 years old, grown in the ground.

Figure 2:
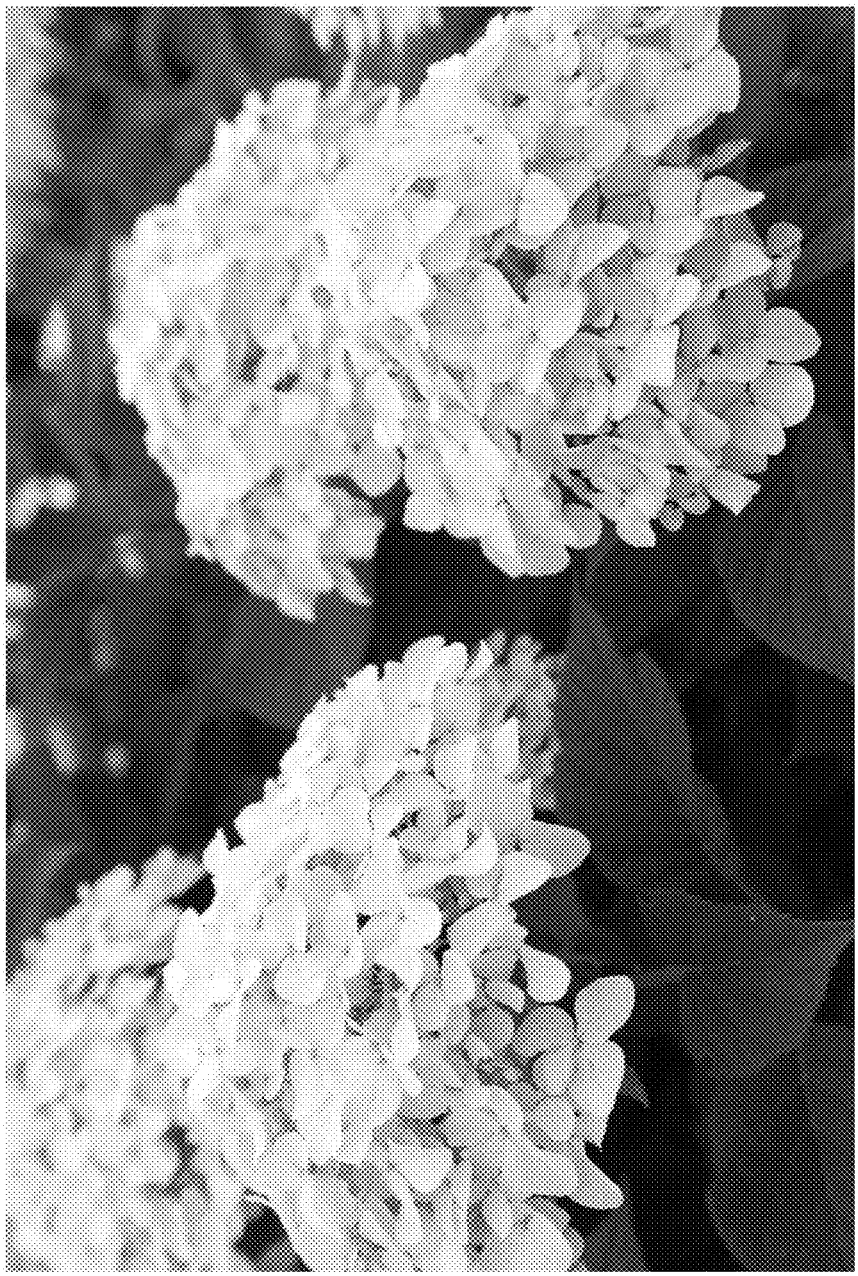

FIG. 2 illustrates in full color a close-up view of typical inflorescences of 'LC NO23'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'LC NO23' plants grown outdoors in Boskoop, the Netherlands. The plants were about 3-years old. Temperatures ranged from about 5° C. to 10° C. at night to 18° C. to 27° C. during the day. No artificial light, photoperiodic treatments were given to the plants. Measurements and numerical values represent averages of typical plant types.

Botanical classification: *Hydrangea arborescens* 'LC NO23'.

PROPAGATION

Typical method: Softwood cuttings.

Roots: Thin, freely branching, fibrous, moderately dense. Off-white in color, not accurately measured with R.H.S. chart.

PLANT

Growth habit: Compact and upright. Deciduous flowering shrub.

Shape: Rounded.

Height: 80 cm.

Plant spread: 128 cm.

Stem:

- *Branching*.—Basal, freely.
- *Number of branches*.—About 30.
- *Shape*.—Round.
- *Color*.—Immature: RHS Yellow-Green 144A and 144B. Mature: RHS Grey-Brown N199A and N199B.
- *Length*.—77 cm.
- *Width*.—7 mm.
- *Strength*.—Very strong.
- *Texture*.—Glabrous.
- *Internode length*.—9 to 10 cm.

FOLIAGE

Leaf:

- *Arrangement*.—Opposite.
- *Shape*.—Broad obovate.
- *Length*.—11 cm.
- *Width*.—8.7 cm.
- *Apex*.—Acuminate.
- *Base*.—Rounded.
- *Margin*.—Serrate. Dense, small serrations.
- *Texture of top surface*.—Slightly pubescent.
- *Texture of bottom surface*.—Slightly pubescent.
- *Color*.—Young Foliage, Upper Side: RHS Yellow-Green 144A, 144B and 144C. Young Foliage, Under Side: RHS Yellow-Green 147C and 147D. Mature Foliage, Upper Side: RHS Yellow-Green 144A, flushed N144A. Mature Foliage, Under Side: RHS Yellow-Green 147C.

Venation:

- *Type*.—Pinnate.
- *Color*.—Mature, Upper Side: RHS Yellow-Green 144B and 144C. Mature, Under Side: RHS Yellow-Green 147C and 147D. 145D towards petiole.

Petiole:

- *Length*.—6 cm.
- *Width*.—2 to 3 mm.
- *Color*.—Upper Side: RHS Greyed-Purple 183A. Under Side: RHS Yellow-Green 145A.
- *Texture*.—Upper Side: Lightly pubescent. Under Side: Lightly pubescent.

INFLORESCENCE

Natural flowering season: June to September.

Inflorescence type: Mophead.

Lastingness: About 8 weeks.

Conspicuousness of fertile flowers: Absent.

Panicle:

- *Shape*.—Semi-flattened globular.
- *Height*.—12 cm.
- *Diameter*.—21 cm.

Fragrance: None.

Sterile flowers:

- *Flowers per inflorescence*.—350 to 400.
- *Aspect*.—Upright.
- *Shape*.—Rotate.
- *Length*.—1.9 cm.
- *Diameter*.—1.9 cm.
- *Persistence*.—Persistent.

Bud:

- *Length*.—2 mm.
- *Diameter*.—1 mm.
- *Shape*.—Ovate.
- *Color*.—RHS Yellow-Green 145C.

Petals: 4 petals, each 1 mm in width and length. Orbicular in shape, glabrous texture. Apex obtuse, base obtuse, margin entire, colored same as the sepals.

Sepals:

- *Number*.—3 or 4.
- *Arrangement*.—Rotate.
- *Shape*.—Ovate.
- *Tip*.—Acute.
- *Base*.—Obtuse.

*Margin*.—Entire.
*Length*.—12 mm.
*Width*.—11 mm.
*Texture*.—Upper side: Glabrous. Under side: Glabrous.
*Color*.—When Opening, Upper Side: RHS Yellow-Green N144A and 144C. When Opening, Under Side: RHS Yellow-Green 144C and 144D. Fully Opened, Upper Side: RHS White NN155A. Fully Opened, Under Side: RHS White NN155A.

Pedicel:
*Length*.—1 cm.
*Diameter*.—1 mm.
*Strength*.—Moderately strong.
*Texture*.—Glabrous.
*Color*.—RHS Yellow-Green 145B and 145C.

Fertile flowers:
*Flowers per inflorescence*.—100.
*Aspect*.—Upright.
*Shape*.—Whorl.
*Length*.—3 mm.
*Diameter*.—3 mm.

Bud:
*Length*.—1.5 mm.
*Diameter*.—1.5 mm.
*Bud shape*.—Globose.
*Bud color*.—RHS Yellow-Green 145C.

Petals:
*Number per flower*.—5.
*Arrangement*.—Rotate.
*Shape*.—Ovate.
*Tip*.—Acute.
*Base*.—Truncate.
*Margin*.—Entire.
*Length*.—1.5 mm.
*Width*.—1.5 mm.
*Texture*.—Upper Side: Glabrous. Under Side: Glabrous.
*Color*.—When Opening, Upper Side: RHS Yellow-Green N144A. When Opening, Under Side: RHS Yellow-Green 144C. Fully Opened, Upper Side: RHS White NN155D. Fully Opened, Under Side: RHS White NN155D.

Sepals: Not observed.

Pedicel:
*Length*.—3 mm.
*Diameter*.—1 mm.
*Texture*.—Slightly pubescent.
*Color*.—RHS Yellow-Green 145B and 145C.

REPRODUCTIVE ORGANS

Sterile flower: Not observed.

Fertile flower:

Stamens:
*Number*.—9 to 10.
*Filament length*.—2 mm.
*Filament color*.—RHS White NN155D.

Anthers:
*Shape*.—Globose.
*Length*.—0.05 mm.
*Color*.—RHS White NN155D.
*Pollen amount*.—None observed.

Pistil:
*Number*.—2.
*Length*.—1 mm.

Stigma:
*Shape*.—Round.
*Color*.—RHS White NN155D.
*Style length*.—0.05 mm.
*Style color*.—RHS White NN155D.
*Ovary color*.—Indistinguishable.

SEEDS

Not observed.

OTHER CHARACTERISTICS

Disease resistance: Neither resistance nor susceptibility to the normal diseases and pests of *Hydrangea* has been observed.

Cold tolerance: Hardy to −15° C.

What is claimed is:

1. A new and distinct cultivar of *Hydrangea* plant named 'LC NO23' as herein illustrated and described.

* * * * *